United States Patent [19]

Ford

[11] Patent Number: 6,127,572

[45] Date of Patent: Oct. 3, 2000

[54] PROCESS FOR PREPARING 2-CARBOXY-5-NITROBENZENESULFONIC ACID AND SALTS THEREOF BY OXIDATION

[75] Inventor: Mark James Ford, Bad Soden, Germany

[73] Assignee: Hoechst Schering AgrEvo GmbH, Berlin, Germany

[21] Appl. No.: 09/135,339

[22] Filed: Aug. 17, 1998

[30] Foreign Application Priority Data

Aug. 19, 1997 [DE] Germany .................... 197 35 879

[51] Int. Cl.[7] .................... C07C 15/16; C07C 315/04
[52] U.S. Cl. ............................ 562/409; 562/430
[58] Field of Search ...................... 562/409, 430

[56] References Cited

U.S. PATENT DOCUMENTS

| 2,675,405 | 4/1954 | Carrara . |
| 3,790,624 | 2/1974 | Massie et al. . |
| 4,608,205 | 8/1986 | Conrow et al. . |
| 5,175,351 | 12/1992 | Rohrscheid . |
| 5,449,812 | 9/1995 | Schnabel et al. . |
| 5,565,608 | 10/1996 | Gless, Jr. et al. . |

FOREIGN PATENT DOCUMENTS

| 149998 | 8/1973 | Czech Rep. . |
| 150000 | 8/1973 | Czech Rep. . |
| 106961 | 9/1897 | Germany . |
| 115410 | 9/1897 | Germany . |
| 4236902 A1 | 5/1994 | Germany . |
| 4334949 A1 | 5/1994 | Germany . |
| 57-200353 | 12/1982 | Japan . |
| WO 94/27959 | 12/1994 | WIPO . |

OTHER PUBLICATIONS

Derwent Abstract No. XP 002084797 published Aug. 8, 1998.
Japanese Chemical Abstract 97:92991.
Chem. Ber., vol. 19 (1886), p. 3238.
Chem. Ber., vol. 30 (1897), p. 3227–3241.
Chem. Ber., vol. 30 (1897), p. 3097–3101.
J. Am. Chem. Soc., vol. 76 (1954), p. 2725–2731.

*Primary Examiner*—Gary Geist
*Assistant Examiner*—Brian J. Davis
*Attorney, Agent, or Firm*—Frommer Lawrence & Haug LLP

[57] ABSTRACT

The invention is directed to a simple process for the preparation of the product 2-carboxy-5-nitrobenzenesulfonic acid (=4-nitro-2-sulfo-benzoic acid) or a salt thereof. The product can be prepared by the oxidation reaction of 2-methyl-5-nitrobenzenesulfonic acid with metal hypochlorites in the presence of metal bases from the group consisting of hydroxides and carbonates, essentially with the exclusion of heavy metal salts.

11 Claims, No Drawings

PROCESS FOR PREPARING 2-CARBOXY-5-NITROBENZENESULFONIC ACID AND SALTS THEREOF BY OXIDATION

BACKGROUND OF THE INVENTION

1. Field of the Invention

The invention relates to the technical field of chemical processes for preparing intermediates which can be employed for preparing active compounds, other intermediates or products intended for use in various areas, for example in the areas of pharmaceutics, crop protection, polymers and/or dyes.

2. Description of the Related Art

The compound 2-carboxy-5-nitrobenzenesulfonic acid is described as an intermediate for the synthesis of various active compounds in U.S. Pat. No. 4,608,205, DE-A-4,334, 949, DE-A4,236,902 and JP-A-57,036,121 and in chemistry handbooks. The preparation of the intermediate can be carried out, for example, by oxidation of 2-methyl-5-nitrobenzenesulfonic acid, and specific mention may be made of the reactions with hot basic potassium permanganate solution (see U.S. Pat. No. 4,608,205) with nitric acid at 130–220° C. (see U.S. Pat. No. 2,675,405), with atmospheric oxygen in the presence of manganese salts and/or cobalt salts (see U.S. Pat. No. 5,175,351, CS-A-149,998, CS 150,000) or with hypochlorite in the presence of heavy metal peroxides and alkali metal hydroxides (see JP-A-57,200, 353). The abovementioned oxidation processes have disadvantages which manifest themselves particularly strongly on scale-up, for example to batches on an industrial scale.

In addition to the problems related to processing and waste which are associated with the handling of large amounts of $KMnO_4$, side reactions occur during this basic oxidation of 2-methyl-5-nitrobenzenesulfonic acid which considerably reduce the yield, such as the well-documented rapid dimerization of the starting material; see Chem. Ber. 1886 (19) 3234, Chem. Berichte 1897 (30) 3236 and J. Am. Chem. Soc. 1954 (76) 2725.

The oxidation with nitric acid, on the other hand, which avoids the base-induced dimerization, is, at the high reaction temperatures required, exothermic to such an extent that its practice on an industrial scale requires considerable control and specific precautions have to be taken to minimise the risk.

The slightly basic oxidations with hypochlorite (JP-57200353) or air (U.S. Pat. No. 5,175,351), however, require heavy metals as catalysts and do likewise have disadvantages, owing to the related expenditure for work-up and waste disposal. Additionally, peroxides may be formed which pose a risk of explosion. A risk of explosion in the abovementioned oxidations with air is also associated with the use of organic solvents on an industrial scale.

It is already known from U.S. Pat. No. 5,565,608 that the isomeric 4-methyl-3-nitrobenzenesulfonic acid (=2-nitro-4-tolyenesulfonic acid) can be readily oxidized on a laboratory scale to give the isomeric 4-carboxyl-3-nitrobenzenesulfonic acid (=2-nitro-4-sulfobenzoic acid) when the oxidation is carried out with NaOCl (sodium hypochlorite) at 50–150° C., preferably at 100–110° C., without heavy metal oxides. Surprisingly, this oxidation does not succeed when the conditions described therein are applied in an analogous manner to 2-methyl-5-nitrobenzenesulfonic acid. Even at temperatures (for example 45–50° C.) below the reaction temperatures required for the oxidation, strong evolution of gas sets in, so that the reaction cannot be carried out in reaction vessels of economically viable size.

At higher temperatures (for example reflux temperature), evolution of gas is reduced, but the oxidation of the sodium or potassium salt of 2-methyl-5-nitrobenzenesulfonic acid with NaOCl under reflux conditions is considerably slower than the decomposition of the reagent. Thus, the reaction with 6 equivalents of aqueous sodium hypochlorite solution (13.5% by weight of NaOCl) gives only 45% conversion to the desired carboxylic acid. As already mentioned, it is additionally known that the oxidation with basic sodium hypochlorite solution gives the dimer 4,4'-dinitrobibenzyl-2,2'-disulfonic acid or 4,4'-dinitrostilbene-2,2'-disulfonic acid as byproducts (see DE-A-115410, DE-A-106961 and Chem. Ber. 1897 (30) 3097).

Other oxidations of methyl-substituted aromatics using sodium hypochlorite are known (see U.S. Pat. No. 3,790,624 and WO-9427959); however, in these oxidations heavy metals are employed as catalysts.

It is therefore an object of the invention to provide a process which allows the oxidation of 2-methyl-5-nitrobenzenesulfonic acid on an industrial scale without the abovementioned disadvantages.

BRIEF DESCRIPTION OF THE INVENTION

The invention provides a process for preparing the compound of the formula (I) or salts thereof

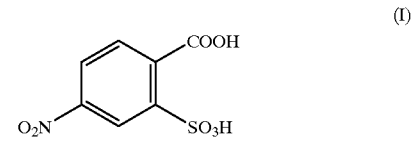

(I)

which comprises oxidizing a compound of the formula (II) or salts thereof

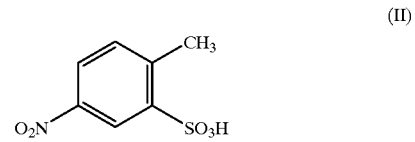

(II)

with a stoichiometric equivalent or an excess of a metal hypochlorite, preferably LiOCl, NaOCl, KOCl or $Ca(OCl)_2$, in the presence of a metal base from the group of the alkali metal hydroxides or alkali metal carbonates or mixtures thereof, essentially with exclusion of heavy metal salts.

DETAILED DESCRIPTION OF THE INVENTION

The stoichiometric equivalent for the oxidation of the methyl group in the compound of the formula (II) are 3 mol of hypochlorite anion or 3 mol of a monovalent hypochlorite per mole of the compound of the formula (II).

Particularly suitable metal bases are the alkali metal hydroxides LiOH, NaOH and KOH and the alkali metal carbonates $Na_2CO_3$ and $K_2CO_3$ and mixures thereof.

The compound of formula (I) is obtained as free carboxybenzenesulfonic acid, as monosalt, disalt or a mixture of the compounds, depending on the pH during work-up. For economical reasons, preference is given to alkali metal and alkaline earth metal salts, in particular to alkali metal salts, such as sodium and potassium salts, and water is employed as solvent to simplify the practice of the reaction.

The process can generally be carried out in such a manner that initially a mixture of compound (II) or a salt thereof, water and the hypochlorite is prepared, for example by addition of 2-methyl-5-nitrobenzenesulfonic acid to at least one equivalent of an alkali metal hydroxide and/or alkali metal carbonate (i.e. at least 1 molar equivalent of base per mole of compound (II), which was mixed beforehand with a stoichiometric equivalent or with an excess, based on compound (II), of an aqueous solution or suspension of the hypochlorite.

Alternatively, the 2-methyl-5-nitrobenzenesulfonic acid can also be added to an aqueous mixture of the hypochlorite, hydroxide and, if appropriate, carbonate, which was obtained by introducing at least a stoichiometric equivalent of chlorine gas, preferably at temperatures of 5° C. or less than 5° C., into an excess of aqueous metal hydroxide and/or metal carbonate. Excess hypochlorite can be recovered from the batch after the oxidation and be transferred to the next batch.

The resulting aqueous mixture, comprising compound (II), hypochlorite, hydroxide and/or carbonate, is then allowed to react with heating, for example heating to 60° C. or more, preferably to 60° C. to reflux (approximately 110° C.). The oxidation reaction can be controlled by adding more base in portions, preferably by adding more aqueous alkali metal hydroxide. If the reaction is controlled by addition of more base, the optimum addition rate depends on the size of the batch and the concentration of the reactants. The addition rate is preferably set such that a pH in the reaction mixture of pH 10 or more than pH 10, for example pH 10 to 11, is ensured.

At a reaction temperature of from 60 to 75° C., the addition of hydroxide or carbonate is usually rate-determining for the course of the reaction, so that an additional determination of the pH may be dispensed with.

At higher reaction temperatures, for example also at reflux temperature, preference is given to maintaining a constant excess of alkali metal hydroxide or alkali metal carbonate, thus ensuring that the total amount of base, for example from 1 to 3 molar equivalents, is already present at the beginning of the reaction.

Alternatively, 2-methyl-5-nitrobenzenesulfonic acid or a salt thereof can be added as a solid, or as a solution or suspension in water, over a period of time of several hours to a mixture of the hypochlorite with the hydroxide and/or the carbonate, while maintaining the abovementioned conditions for the pH and, if appropriate, adding more base.

The hypochlorite is employed in a stoichiometric equivalent or in excess, preferably in a total amount of from 3 to 10 molar equivalents, in particular from 4 to 7 molar equivalents, of hypochlorite per mole of compound of the formula (11); the total amount of hypochlorite may, for example, be added even at the beginning of the reaction, or it results from the sum of the proportions which were added a little at a time or constantly over the entire reaction time, an excess of hypochlorite relative to the compound of the formula (II) preferably being maintained at all times. The excess of hypochlorite can also be achieved by introducing chlorine gas into the alkaline reaction solution.

From a technical point of view, the oxidation process can be carried out in a simple manner, and it affords the product (I) in excellent yields and purities. During practice, neither evolution of gas nor decomposition of the hypochlorite, as observed during the analogous use of the process conditions of U.S. Pat. No. 5,565,608 (=without the addition of base) in the oxidation of the compound of the formula (II), takes place.

Work-up of the crude product can be carried out by customary methods of laboratory practice or process engineering. After the oxidation, the product of the formula (I) is initially present as monosalt or disalt, preferably as disodium or dipotassium salt, which can be isolated directly by filtration, if appropriate after salting out.

Alternatively, the product can be obtained after acidification with an acid, preferably a mineral acid, such as hydrochloric acid or sulfuric acid, as monosalt, preferably, owing to the low solubility, as potassium salt or sodium salt or as a mixture thereof or else as free acid, depending on the pH which is set.

Crystallization and recovery of the product as mono- or disalt can be facilitated by addition of a water-soluble salt of an alkali metal or alkaline earth metal hydroxide.

Advantageously, some of the excess oxidizing agent is recovered as hypochlorite and recycled. For this purpose, the reaction medium is acidified, either before or after isolation of the product, and the chlorine gas that is formed from excess hypochlorite is introduced into an alkaline solution, for example into aqueous alkali metal hydroxide, or a solution of alkali metal hydroxide and aqueous alkali metal hypochlorite, which, if appropriate, contains starting material or oxidation product.

The invention also provides the use of the compounds of the formula (I) prepared in accordance with the invention for preparing processed products, preferably in the technical areas mentioned at the outset. Also provided are the processes for preparing processed products of the compounds (I), preferably those having a partial structure of the formula (IIIa) or (IIIb),

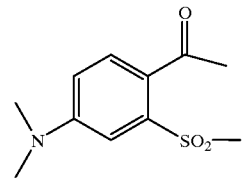

(IIIa)

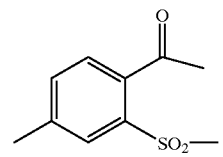

(IIIb)

where the free bonds denote the binding sites of the partial structure (not to be confused with the short notation for methyl groups which is sometimes used), which comprise carrying out the process according to the invention for preparing the compounds (I) which is further illustrated above in a process step.

In the examples below, percentages are based on weight, unless defined otherwise.

EXAMPLES

Variant A 1 kg of 79.8% strength 2-methyl-5-nitrobenzenesulfonic acid (3.67 mol) was added to a mixture of 371 ml of 40% strength aqueous potassium hydroxide (3.70 mol) and 10.5

1 (22.35 mol) of aqueous sodium hypochlorite. The resulting suspension was heated to 65° C. and, at this temperature, admixed with 768 ml of 40% strength aqueous potassium hydroxide (7.67 mol) at a rate of 1.07 ml/min. After the addition was complete, stirring was continued at 65° C. for another 4 hours, and 1.4 kg (18.78 mol) of potassium chloride were then added. After cooling to 50–60° C., the mixture was acidified dropwise with concentrated hydrochloric acid (37% strength, 920 ml, 11.1 mol) at 50–60° C. over a period of 1 to 2 hours, and the chlorine gas that was formed in the process was trapped in excess aqueous potassium hydroxide. After cooling to 15–20° C. while passing through nitrogen gas, thus removing remaining chlorine gas, and after further stirring at 15–20° C. for 30 to 60 min, the product 2-carboxy-5-nitrobenzenesulfonic acid monopotassium salt was isolated by filtration and dried at 75° C./100 mbar. The product was obtained as a white powder; yield: 1101 g; 86.7% pure product (91.3% of theory).

Variant B 27.2 g of 79.8% strength 2-methyl-5-nitrobenzenesulfonic acid (0.1 mol) were added to a mixture of 10.1 ml of 40% strength aqueous potassium hydroxide (0.1 mol) and 141 ml (0.3 mol) of aqueous sodium hypochlorite. The resulting suspension was heated to 65° C. and, at this temperature, admixed with 23 ml of 40% strength aqueous potassium hydroxide (0.23 mol) at a rate of 0.04 ml/min. After the addition was complete, the mixture was cooled to 0° C. and then admixed with 12.24 g (0.3 mol) of KOH. Over a period of 30 min, 10.64 g (0.15 mol) of chlorine gas were then introduced at this temperature. The temperature was then increased to 65° C., aqueous KOH (40% strength, 9.0 ml, 0.9 mol) was added at 0.04 ml/min and the mixture was subsequently stirred at 65° C. for another 2 hours. After cooling to 50° C., the mixture was acidified dropwise with concentrated hydrochloric acid (37% strength, 18 ml, 0.22 mol) at 50° C. over a period of 1 hour, cooled to 15–20° C. while passing through nitrogen gas, thus removing remaining chlorine gas, and stirred at 15–20° C. for another 2 hours. The product 2-carboxy-5-nitrobenzenesulfonic acid monopotassium salt was obtained, after filtration and drying at 75° C./100 mbar as a white powder; yield: 31 g; 76.5% pure product (83.1 % of theory).

Variant C

2-Methyl-5-nitrobenzenesulfonic acid (79.8% strength, 40.8 g, 0.15 mol) was added to a mixture of 32 ml of 40% strength aqueous KOH (0.32 mol), 40.8 g (0.3 mol) of $K_2CO_3$ and 420 ml (0.71 mol) of aqueous NaOCl. With vigorous stirring, the resulting suspension was heated to 85° C. and kept at 85° C. for 30 minutes, heated at 90° C. for 30 minutes and then heated at reflux (103–104° C.) for 3.5 hours.

The reaction mixture was then cooled to 15–20° C. and stirred at this temperature for another 30 min.

After filtration and drying at 75° C./100 mbar, a cream-colored powder was obtained in a yield of 42.8 g of 94.9% pure 2carboxy-5-nitrobenzene-sulfonic acid monosodium monopotassium disalt (88.2% of theory).

I claim:

1. A process for preparing the compound of the formula (I) or salts thereof,

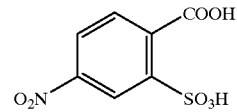

(I)

which comprises oxidizing a compound of the formula (II) or salts thereof

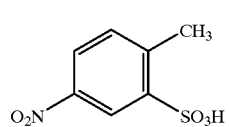

(II)

with a stoichiometric equivalent or an excess of a metal hypochlorite in the presence of a metal base from the group of the alkali metal hydroxides or mixtures thereof or alkali metal carbonates, essentially with exclusion of heavy metal salts.

2. The process as claimed in claim 1, wherein a metal hypochlorite from the group consisting of LiOCl, NaOCl, KOCl and Ca(OCl)$_2$ and mixtures thereof is used.

3. The process as claimed in claim 1, wherein an alkali metal hydroxide from the group consisting of LiOH, NaOH and KOH and mixtures thereof is used.

4. The process as claimed in claim 1, wherein an alkali metal carbonate from the group consisting of Na$_2$CO$_3$ and K$_2$CO$_3$ and mixtures thereof is used.

5. The process as claimed in claim 1, wherein the process is carried out in the presence of water.

6. The process as claimed in claim 1, wherein the oxidation reaction is carried out at from 60 to 110° C.

7. The process as claimed in claim 1, wherein an excess of metal hypochlorite is prepared or maintained by introducing chlorine gas into the alkaline reaction solution.

8. The process as claimed in claim 1, wherein from 3 to 10 molar equivalents of hypochlorite are employed per mole of compound of the formula (II).

9. The process as claimed in claim 1, wherein the excess oxidizing agent or a part thereof is recovered from the reaction mixture after the oxidation as hypochlorite.

10. A process for the preparation of processed products from compounds of the formula (I) which comprises the process as claimed in claim 1.

11. The process as claimed in claim 10, wherein the processed products are active compounds, intermediates or products intended for use in the areas of pharmaceuticals, crop protection, polymers and dyes.

* * * * *